United States Patent [19]

Krause et al.

[11] 4,082,953
[45] Apr. 4, 1978

[54] DENTAL X-RAY DIAGNOSTIC DEVICE

[75] Inventors: Hartmut Krause, Erlangen; Ulrich Grassmé, Nuremberg, both of Germany

[73] Assignee: Siemens Aktiengesellschaft, Berlin & Munich, Germany

[21] Appl. No.: 681,527

[22] Filed: Apr. 29, 1976

[30] Foreign Application Priority Data

May 2, 1975 Germany .............................. 2519640
Jan. 8, 1976 United Kingdom .............. 00706/76

[51] Int. Cl.$^2$ ............................................. H05G 1/30
[52] U.S. Cl. ...................................... 250/413; 250/478
[58] Field of Search ............... 250/322, 402, 413, 490, 250/478, 479

[56] References Cited

U.S. PATENT DOCUMENTS

| | | | |
|---|---|---|---|
| 3,103,590 | 9/1963 | Berglund et al. | 250/413 |
| 3,432,657 | 3/1969 | Slavin | 250/490 |
| 3,600,584 | 8/1971 | Schneble | 250/413 |
| 3,792,267 | 2/1974 | Westerkowsky | 250/402 |

*Primary Examiner*—Bruce C. Anderson
*Attorney, Agent, or Firm*—Hill, Gross, Simpson, Van Santen, Steadman, Chiara & Simpson

[57] ABSTRACT

A dental X-ray diagnostic device for the preparation of X-ray film pictures in which an X-ray radiation element is located exterior to the patient. A film holder is inserted into the mouth of the patient, and means is provided for setting the exposure time for switching off the X-ray tube high voltage upon reaching the dosage corresponding to optimum blackening of the film. An automatic exposure arrangement measures the exposure time and has a radiation detector attached to the film holder which is connected to a wireless transmitter. An antenna connected to a receiver, receives the transmitted signals and controls the switching circuit for switching off the X-ray high voltage supply. The transmitter is preceded by an integrator for a signal corresponding to the detector signal. A threshold switching circuit has a threshold selected so that upon reaching the dosage corresponding to optimum film blackening, it switches and applies a control signal to the transmitter.

8 Claims, 3 Drawing Figures

DENTAL X-RAY DIAGNOSTIC DEVICE

BACKGROUND OF THE INVENTION

There are already known in the art dental X-ray diagnostic devices provided with an X-ray radiator exterior to the patient and a film holder to be introduced into the mouth of the patient, and means for determining the exposure time. It is already known how to use a timer switch or an mAs relay for setting the exposure time.

A timer switch or an mAs relay must be set by hand in order to determine the exposure time. The operator must estimate and set the required exposure time or the required mAs product on the basis of the patient's condition. Faulty exposures are possible. Therefore, with the trend toward automation, it is desirable to automatically set the exposure time for a dental X-ray diagnostic device, i.e., to use an automatic exposure circuit.

It is, therefore, an object of the present invention to provide a dental X-ray diagnostic device for the preparation of X-ray film pictures, with an X-ray radiator exterior to a patient and a film holder which can be introduced into the mouth of the patient, and means for measuring and setting the exposure time which contains a switching device for switching off the X-ray tube high voltage upon reaching the dosage corresponding to the optimum film blackening.

Another object of the present invention is to provide a dental X-ray diagnostic device of the foregoing character in which this device comprises an automatic exposure circuit for setting the exposure time whose individual parts bother neither the operator nor the patient during operation.

A further object of the present invention is to provide an X-ray diagnostic device, as described, which may be economically fabricated and which has a substantially long operating life.

SUMMARY OF THE INVENTION

The objects of the present invention are achieved by providing that for setting the exposure time, there is present an automatic exposure system (circuit) having a radiation detector attached to a film holder. The film holder is connected to a wireless transmitter. An antenna for receiving the transmitter signals is connected to a receiver which controls the switching device for shutting off the X-ray tube high voltage. It is essential to the invention that the detector of the automatic exposure system is not connected to the associated circuit via a cable introduced into the mouth of the patient. Instead, the coupling between the detector and the circuit elements located outside the mouth of the patient should be wireless.

In an embodiment of the present invention the transmitter is preceded by an integrator for a signal corresponding to the detector signal. A threshold switch is provided with threshold that can be chosen so that upon reaching the dosage corresponding to an optimal film blackening, it switches and applies a control signal to the transmitter. This embodiment is based on the condition that with a dental X-ray diagnostic device only one X-ray tube voltage and only one X-ray tube current is used, so that the output signal of the integrator is a measure of the radiation dosage acting on the film and of the film blackening. Modulating the frequency emitted by the transmitter is not required. Such a modulation takes place with an embodiment where the transmitter has means for modulating the frequencies emitted by it and which are controlled by a signal corresponding to the detector output signal. However, the circuit complexity with the circuit elements preceding the transmitter, is less than with the embodiment described above.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
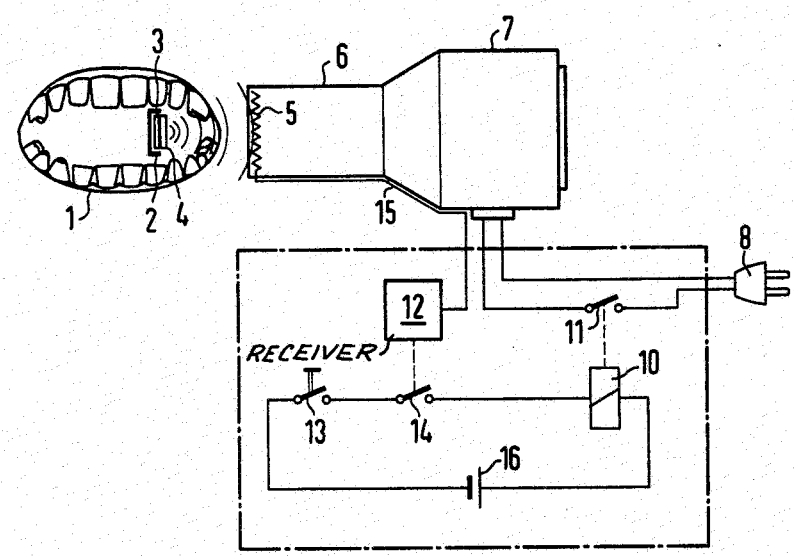
FIG. 1 is a view of a dental X-ray diagnostic device in accordance with the present invention.

In FIG. 1, the schematically shown mouth 1 of a patient carries a film holder 2 which, in a pocket 3, carried a dental X-ray film. Adjacent to pocket 3 is a detector-transmitter circuit 4 which transmits a wireless electrical signal in accordance with the film blackening. This signal is received by an antenna 5 which is attached to the end of a tube 6. The tube 6 is connected to a housing 7 which holds an X-ray tube and the associated high-voltage transformer. The antenna 5 has a short distance from the detector-transmitter circuit 4 so that low transmitter power is sufficient. The high-voltage transformer can be connected via a plug 8 to the power supply line. It has a circuit arrangement which determines the exposure time and which includes a switching relay 10 with a contact 11, a receiver 12, an exposure triggering switch 13 and a switch 14 actuated by receiver 12. Such receivers are well known for medical telemetry and a typical receiver useful for the system of this invention is described in "Bio-Medical Telemetry", R. Stuart Mackay, 1970, John Wiley & Sons, Inc., Figure 11.2 at page 264.

The detector-transmitter circuit 4 is an integrated module. Such transmitter circuits for telemetry are well known and an example of such a device is shown in "Bio-Medical Telemetry", R. Stuart Mackay, 1970, John Wiley & Sons, Inc., Figure 8.2 at page 188. When placed on the dental X-ray film, it is switched on, and upon attaining the dosage corresponding to the desired film blackening, is turned off again. When it emits radiation, the receiver 12, which is connected to the antenna 5 via line 15, closes contact 14. If the exposure trigger switch 13 is closed, the power source is connected to the relay 10 which switches the X-ray tube on. After the desired dosage has acted on the X-ray film, the radiation of detector-transmitter circuit 4 disappears, the receiver 12 opens its contact 14, and the relay opens its contact 11, so that the X-ray tube is disconnected again.

Figure 2:
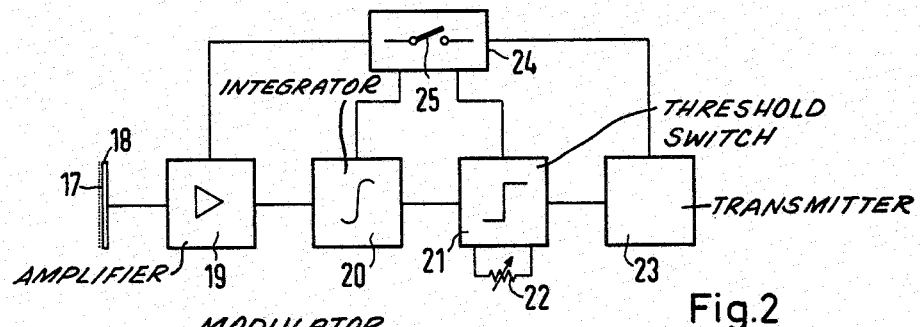
FIG. 2 shows an embodiment of the detector-transmitter circuit in the device of FIG. 1.

FIG. 2 shows that the curcuit 4 has a luminous layer 17 behind which a light-sensitive detector 18 is located. The luminous layer 17 is made luminous by the X-ray radiation acting on the X-ray film so that the output signal of detector 18 is a measure of the radiation intensity. This output signal is amplified in an amplifier 19 and is integrated in the integrator 20. The integrator 20 is followed by a switching circuit 21 as, for example, a Schmitt trigger, whose threshold can be set by means of a nominal-frequency selector 22 in accordance with the film sensitivity. The threshold switching circuit 21 controls the switching on and off of transmitter 23. Circuit elements 19 through 23 are supplied by a power supply 24 which includes a switch 25 by means of which the operating voltage can be applied to circuit elements 19 through 23. the amplifier 19, integrator 20 and threshold switching circuit 21 are well known devices and examples of the same are shown in "Handbook of Integrated Circuit Operational Amplifiers", George B. Rutkowski, 1975, Prentice-Hall. Pages 155 through 158 describe an amplifier useful as the amplifier 19 in this application. Pages 166 through 169 illustrate an integrator useful for the integrator 20 of the inventive system. Finally, pages 201 and 202 illustrate a comparator useful as the threshold switch 21 for the system of this invention.

In order to take an X-ray picture, switch 25 is closed so that transmitter 23 is turned on. This causes receiver 12 to close its contact 14. When X-ray radiations occur, the output signal of amplifier 19, which corresponds to the radiation intensity, is integrated in integrator 20. Upon reaching the dosage set by the nominal frequency selector 22 and corresponding to the optimal film blackening, the switching circuit 21 turns off transmitter 23, so that the receiver 12 opens its contact 14 and terminates the exposure.

In place of luminous layer 17 and the light-sensitive detector 18, one may directly use a detector sensitive to X-rays.

Figure 3:
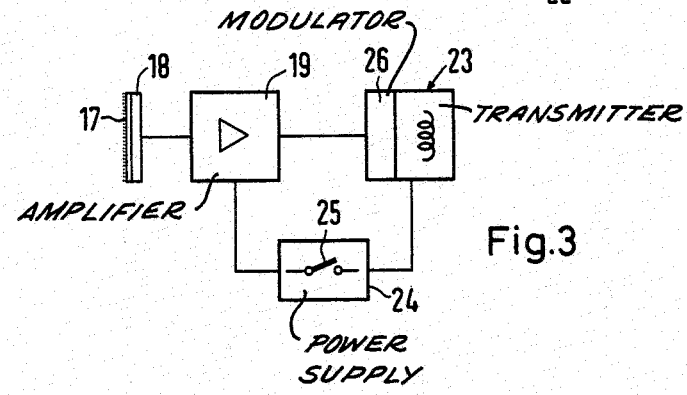
FIG. 3 shows another embodiment of the detector-transmitter circuit.

In the embodiment of FIG. 3, the amplifier 19 is directly connected to the transmitter 23. Hence, circuit elements 20 and 21 of FIG. 2 are not present. The transmitter 23 contains a modulation device 26 which modulates the emitted radiation of the transmitter as a function of the output signal of detector 18, so that this signal is a measure of the radiation intensity. With this embodiment, circuit elements 20 and 21 may be located in the receiver 12. Thus, in this case the receiver 12 integrates the signal that is received and, upon reaching a preset limit, causes it to be turned off. The detector-transmitter circuit of FIG. 3 is of simpler design than that of the arrangement of FIG. 2, and therefore it can be more easily accomodated in the mouth of a patient.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

We claim:

1. A dental X-ray diagnostic device for preparation of X-ray film pictures comprising, in combination, X-ray radiation means with an X-ray tube and high-voltage supply therefor exterior to a patient; film holding means insertable into the mouth of the patient; means for setting the exposure time and having switching means for switching off the X-ray tube high voltage upon reaching the dosage corresponding to optimum blackening of film in said film holding means; said setting means comprising automatic exposure means for measuring the exposure time and having a radiation detector attached to said film holding means, a wireless transmitter connected to said film holding means, and an antenna for receiving signals from said transmitter, and a receiver connected to said antenna and controlling said switching means for switching off the X-ray tube high voltage supply.

2. The dental X-ray diagnostic device as defined in claim 1, including integrating means connected in front of said transmitter for integrating the detected signal; threshold switching means connected to the output of said integrating means for applying a control signal to said transmitter when the dosage corresponding to optimum film blackening is reached.

3. The dental X-ray diagnostic device as defined in claim 2, including means for switching off said transmitter by the control signal of said threshold switching means.

4. The dental X-ray diagnostic device as defined in claim 2, including manually operable setting means connected to said threshold switching means for selectively setting the threshold level of said threshold switching means.

5. The dental X-ray diagnostic device as defined in claim 1, wherein said transmitter has frequency modulating means for modulating the frequency of the signal transmitted by said transmitter, and means for controlling said modulating means by a signal corresponding to the detected signal from said receiver.

6. The dental X-ray diagnostic device as defined in claim 1, wherein said receiver comprises a light-sensitive detector and an adjoining luminous layer.

7. The dental X-ray diagnostic device as defined in claim 1, wherein said receiver comprises an X-ray sensitive detector.

8. The dental X-ray diagnostic device as defined in claim 1 including a housing for said X-ray tube, said antenna being located on the end facing the patient of the X-ray tube which is connected to said housing.

* * * * *